(12) United States Patent
Nilsen et al.

(10) Patent No.: US 7,684,589 B2
(45) Date of Patent: Mar. 23, 2010

(54) METHOD AND APPARATUS FOR IMAGE RECONSTRUCTION USING DATA DECOMPOSITION FOR ALL OR PORTIONS OF THE PROCESSING FLOW

(75) Inventors: Roy Arnulf Nilsen, Waukesha, WI (US); Evgeny Drapkin, Delafield, WI (US); Mary Sue Kulpins, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 12/367,627

(22) Filed: Feb. 9, 2009

(65) Prior Publication Data

US 2009/0169085 A1 Jul. 2, 2009

Related U.S. Application Data

(63) Continuation of application No. 10/999,347, filed on Nov. 30, 2004, now Pat. No. 7,489,799.

(51) Int. Cl.
*G06K 9/00* (2006.01)
*A61B 6/00* (2006.01)
*A61B 5/05* (2006.01)

(52) U.S. Cl. ............................ 382/100; 378/4; 600/425

(58) Field of Classification Search ................. 382/128, 382/129, 130, 131, 132, 133, 134, 254; 378/4, 378/6, 21, 23, 24, 25, 26, 27, 901; 128/920, 128/922; 600/407, 410, 411, 412, 425
See application file for complete search history.

(56) References Cited

U.S. PATENT DOCUMENTS

| | | | | |
|---|---|---|---|---|
| 5,970,111 A | * | 10/1999 | Samarasekera et al. | 378/4 |
| 5,987,094 A | * | 11/1999 | Clarke et al. | 378/62 |
| 6,044,125 A | * | 3/2000 | Flohr et al. | 378/4 |
| 6,081,612 A | * | 6/2000 | Gutkowicz-Krusin et al. | 382/128 |
| 6,169,817 B1 | * | 1/2001 | Parker et al. | 382/131 |
| 7,139,416 B2 | * | 11/2006 | Vuylsteke | 382/128 |
| 2005/0207630 A1 | | 9/2005 | Chan et al. | |

* cited by examiner

*Primary Examiner*—Abolfazl Tabatabai
(74) *Attorney, Agent, or Firm*—Dean D. Small; Small Patent Law Group

(57) ABSTRACT

A method and apparatus for processing raw image data to create processed images. Raw image data is acquired. The raw image data is decomposed by a data decomposer into N subsets of raw image data. The number N is based on a number of available image generation processors. The N subsets of raw image data are processed by at least one image generation processor to create processed image data. If more than one image generation processor is available, the image generation processors perform image processing on the raw image data in parallel with respect to each other.

18 Claims, 5 Drawing Sheets

METHOD AND APPARATUS FOR IMAGE RECONSTRUCTION USING DATA DECOMPOSITION FOR ALL OR PORTIONS OF THE PROCESSING FLOW

CROSS REFERENCE TO RELATED APPLICATIONS

The present application is a continuation application of U.S. patent application Ser. No. 10/999,347, filed Nov. 30, 2004, which is hereby incorporated by reference in its entirety.

BACKGROUND OF THE INVENTION

This invention relates generally to processing and image reconstruction based on acquired raw image data. In particular, the present invention relates to increasing the processing performance with respect to the image reconstruction of diagnostic image data.

Raw image data from various diagnostic medical systems, such as Computed Tomography (CT) and Positron Emission Tomography (PET) systems, is acquired for diagnostic purposes. The CT and PET systems need to be able to support numerous scanning and reconstruction modes. The associated reconstruction algorithms are complex and computationally intensive. Users of the diagnostic medical systems desire an improvement in image quality, along with minimizing the time required to generate images based on raw image data and improving the reliability of the reconstruction process. By decreasing the amount of time needed to generate the desired images from raw image data, images can be evaluated sooner and patient through-put may be improved.

Previous diagnostic systems used different specialized processing units to accomplish specific tasks. That is, the reconstruction process was broken down according to the steps to be done. The processing units may operate in parallel or serially with respect to each other. In order to add processing capability, however, new processing units had to be added and the system design reconfigured and/or coordinated to integrate the new units and steps, both increasing the complexity and limiting the flexibility of the diagnostic system. Scalability and increased performance are thus difficult to achieve when adding additional processing units.

Thus, an apparatus and method are desired to reconstruct image data that addresses the problems noted above and others previously experienced.

BRIEF DESCRIPTION OF THE INVENTION

In one embodiment, a method for generating images. Raw image data representative of an object of interest is acquired. The raw image data is decomposed into N subsets of raw image data. N is based on a number of available image generation processors. The N subsets of raw image data are processed to create processed image data. The image generation processors perform image processing on the image data in parallel with respect to each other.

In another embodiment, a method for increasing the performance of a system for processing raw image data. Raw image data is acquired which is representative of an object of interest. The raw image data is divided into substantially equal subsets of raw image data. At least one of the substantially equal subsets of raw image data is processed with an image generation processor.

In another embodiment, a scalable apparatus for processing raw image data. A data decomposer divides raw image data which is acquired by a data acquisition system. At least two image generation processors process the raw image data in parallel with respect to each other.

DETAILED DESCRIPTION OF THE INVENTION

Figure 1:
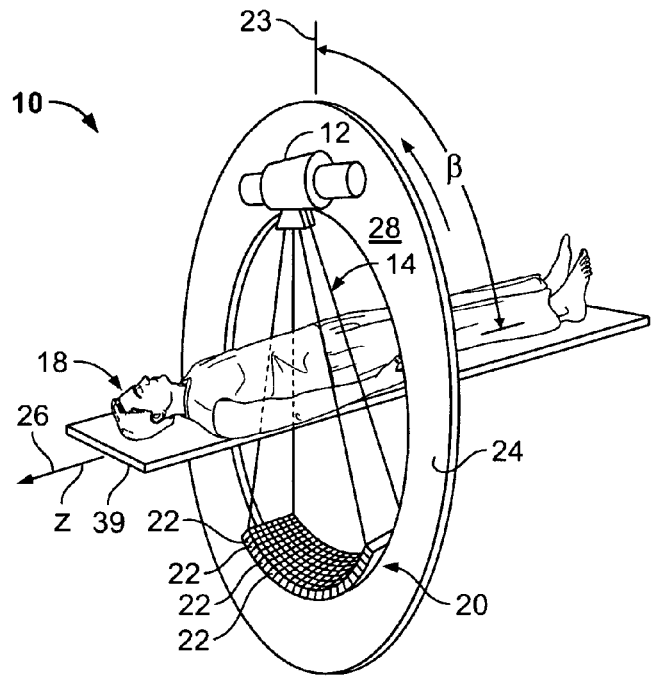
FIG. 1 illustrates a computed tomography (CT) imaging system formed in accordance with an embodiment of the present invention.

FIG. 1 illustrates a CT imaging system 10 formed in accordance with an embodiment of the present invention. The CT imaging system 10 includes an x-ray source 12 oriented to project a cone beam 14 of x-rays from a focal spot 16 (FIG. 2) through a patient 18 to be received by a two-dimensional detector array 20. The two-dimensional detector array 20 includes a number of detector elements 22 arranged over the area of the detector array 20 in generally perpendicular columns and rows to detect a projected image of the x-rays 14 passing through the patient 18. The rows of detector elements 22 may extend along an in-slice dimension. By way of example only, each row may include 1,000 separate detector elements 22, and the array 20 may include 16 rows disposed along the slice dimension. The detectors 22 may be gas or solid state detectors which produce an electrical signal proportional to the x-ray flux received over the sample period.

The x-ray source 12 and the two-dimensional detector array 20 are mounted on either side of a gantry 24 so as to rotate about an axis of rotation 26 generally positioned within the patient 18. The axis of rotation 26 forms the z-axis of a Cartesian coordinate system having its origin centered within the cone beam 14. The plane defined by the x and y axis of this coordinate system thus defines a plane of rotation, specifically the gantry plane 28 of the gantry 24.

Figure 2:
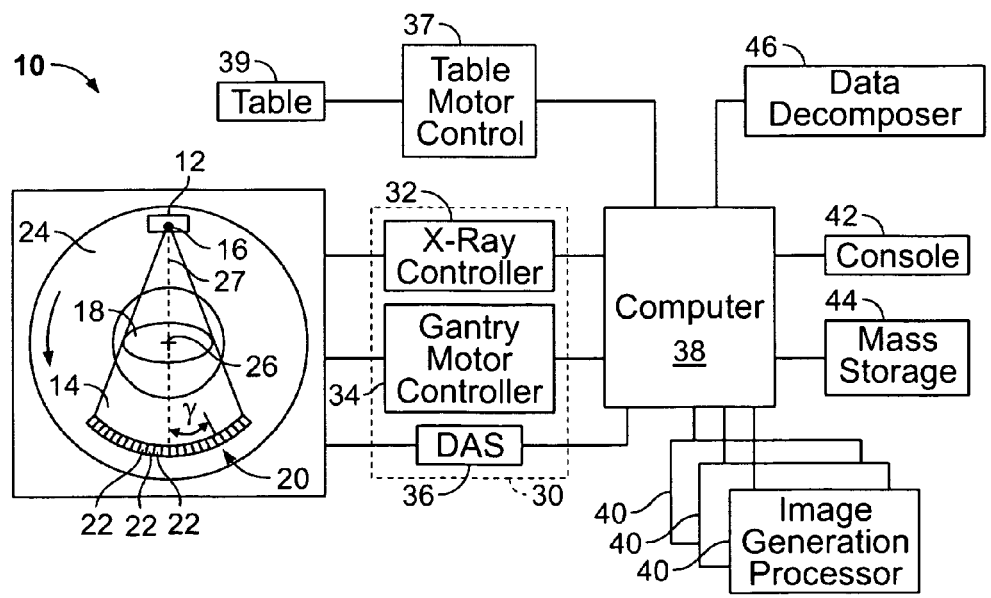
FIG. 2 illustrates a block diagram of the CT imaging system formed in accordance with an embodiment of the present invention.

FIG. 2 illustrates a block diagram of the CT imaging system 10 formed in accordance with an embodiment of the present invention. The control subsystem of the CT imaging system 10 has gantry associated control modules 30 which include: x-ray controller 32, which provides power and timing signals to the x-ray source 12, gantry motor controller 34, which controls the rotational speed and position of the gantry 24. A data acquisition system (DAS) 36 receives raw image data from the two-dimensional detector array 20 and converts the data into digital form for later computer processing. The x-ray controller 32, the gantry motor controller 34 and the data acquisition system 36 are connected to computer 38. The computer 38 also governs operation of a table motor control 37 which drives a motor that moves the patient table 39 along the z-axis 26.

The computer 38 is a general purpose minicomputer programmed to acquire and manipulate projection data. The computer 38 is connected to a data decomposer 46 and one or more image generation (IG) processors 40. The data decomposer 46 sends raw image data to the IG processors 40 which process raw image data as discussed below. In FIG. 2, three IG processors 40 are illustrated, although it should be understood that more or less than three IG processors 40 may be utilized by the CT imaging system 10.

The computer 38 receives commands and scanning parameters via operator console 42 which is generally a CRT display and keyboard that enables an operator to enter parameters for the CT scan and to display the reconstructed image. A mass storage device 44 provides a means for storing operating programs.

During data acquisition, the CT imaging system 10 functions as a conventional cone-beam system in gathering data. In the step-and-shoot acquisition method, the table 39 is held stationary as the x-ray emitter 12 and detector array 20 make a complete revolution around the gantry 24 about the axis of rotation 26. At each of a plurality of angular positions β, the attenuation data from all the detectors 22 in array 20 are stored in the mass memory 44. Upon completion of a full rotation, the computer 38 commands the table motor control 37 to advance the table 39 to another position along the z-axis 26 and another rotational scan of the patient 18 is performed. This process is repeated until the desired portion of the patient 18 has been fully scanned. Alternatively, the CT imaging system 10 may acquire data in the helical acquisition mode, wherein the table motor control 37 advances the table 39 as the x-ray emitter 12 and detector array 20 are rotated and scan data is being acquired.

Figure 3:
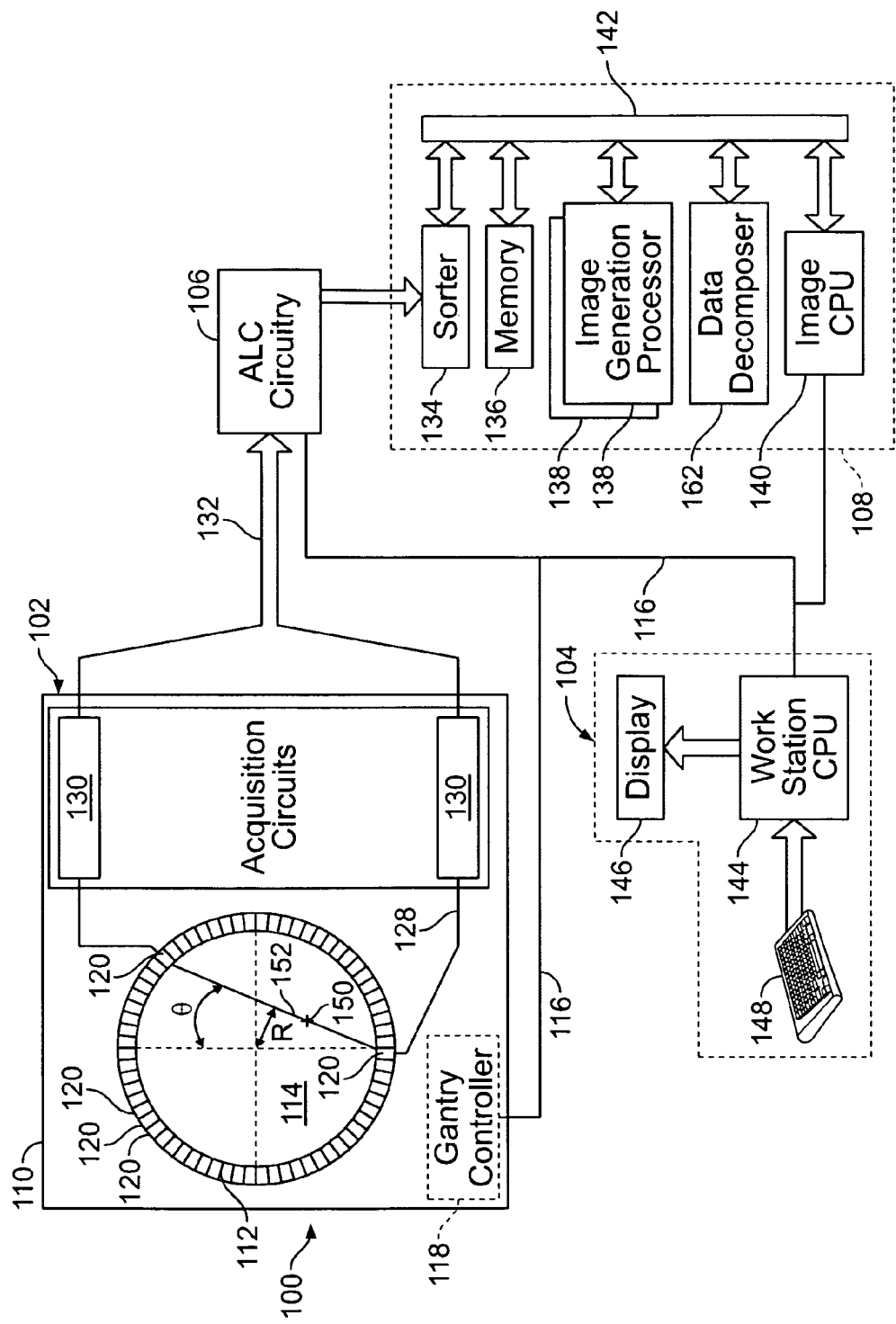
FIG. 3 illustrates a Positron Emission Tomography (PET) scanner system formed in accordance with an embodiment of the present invention.

FIG. 3 illustrates a Positron Emission Tomography (PET) scanner system 100 formed in accordance with an embodiment of the present invention. The PET scanner system 100 includes an acquisition system 102, an operator work station 104, acquisition, locator and coincidence (ALC) circuitry 106, and image reconstruction components 108.

The PET scanner system 100 includes a gantry 110 which supports a detector ring assembly 112 about a central bore which defines an imaging area 114. A patient table (not illustrated) is positioned in front of the gantry 110 and is aligned with the imaging area 114. A patient table controller (not shown) moves a table bed into the imaging area 114 in response to commands received from the operator work station 104 through a serial communications link 116.

A gantry controller 118 is mounted within the gantry 110 and is responsive to commands received from the operator work station 104 through the communication link 116 to operate the gantry 110. For example, the gantry 110 may perform a "coincidence timing calibration scan" to acquire corrective data, or an "emission scan" in which positron annihilation events are counted.

Figure 4:
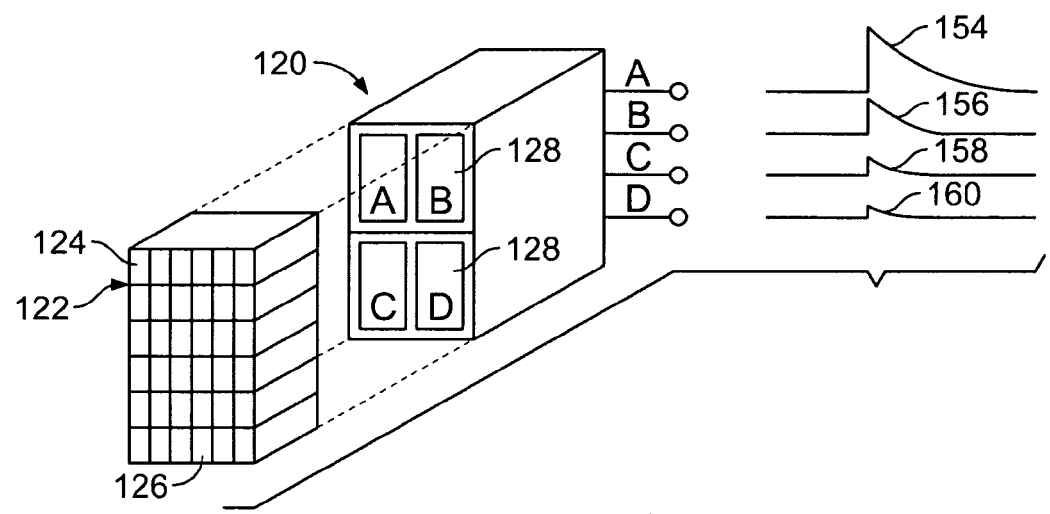
FIG. 4 illustrates a detector unit and associated PMT signals in accordance with an embodiment of the present invention.

FIG. 4 illustrates a detector unit 120 and associated PMT signals in accordance with an embodiment of the present invention. The detector ring assembly 112 comprises a large number of detector units 120. Although not illustrated, detector units 120 are arranged in modules, each module including six separate and adjacent detector units 120. A typical detector ring assembly 112 includes 56 separate modules such that each detector ring assembly 112 includes 336 separate detector units 120. Each detector unit 120 may include a set of bismuth germinate (BGO) scintillator crystals 122, such as crystals 124 and 126, arranged in a 6×6 matrix and disposed in front of four photo multiplier tubes (PMTs) A, B, C and D which are collectively referred to by numeral 128. When a photon impacts a crystal 122, a scintillation event occurs and the crystal generates light which is directed at PMTs 128. Each PMT 128 receives at least some light generated by the scintillation event and produces an analog signal 154-160 which arises sharply when a scintillation event occurs and then tails off exponentially with a time constant of approximately 300 nanoseconds. The relative magnitudes of the analog signals 154-160 are determined by the position in the 6×6 BGO matrix at which a scintillation event takes place, and the total magnitude of these signals is determined by the energy of a photon which causes the event.

Returning to FIG. 3, a set of acquisition circuitry 130 is mounted within the gantry 110 to receive the four analog signals 154-160 from each detector unit 120 in the assembly 112. The acquisition circuitry 130 provides analog signals 154-160 to ALC circuitry 106 via a data bus 132. The ALC circuitry 106 uses the analog signals 154-160 to determine the energy of a detected event, whether the energy detected likely corresponds to a photon, the actual coordinates of a detected event within the block of scintillation crystals 122, the time of the event (i.e. generates a time stamp) and compares event times to identify coincidence pairs of events that are stored as coincidence data packets. Each coincidence data packet includes a pair of digital numbers which precisely identify the addresses of the two scintillation crystals 122 that detected an associated event.

Image reconstruction components 108 includes a sorter 134, a memory module 136, one or more IG processors 138, a data decomposer 162, an image CPU 140 and a backplane bus 142 which conforms to the VME standards and links all other processor components together. In FIG. 3, two IG processors 138 are illustrated, although it should be understood that more or less than two IG processors 138 may be utilized by the PET scanner system 100. The primary purpose of sorter 134 is to generate memory addresses for the coincidence data packets to efficiently store coincidence data. The set of all projection rays that point in the same direction and pass through the PET scanner's FOV is a complete projection, or "view". A distance R between a particular projection ray and a center of the FOV locates that projection ray within the FOV. As shown in FIG. 3, for example, a positron annihilation (hereinafter an "event") 150 occurs along a projection ray 152 which is located in a view at the projection angle θ and the distance R. The sorter 134 counts all of the events 150 which occur on this projection ray (R, θ) during an acquisition period by sorting out the coincidence data packets that indicate an event at the two BGO detector crystals lying on the projection ray 152.

During a data acquisition, the coincidence counts are organized in memory 136 as a set of two-dimensional arrays, one for each axial image, and each having as one of its dimensions the projection angle θ and the other dimension the distance R. The θ by R array of detected events is called a histogram. Coincidence events occur at random and the sorter 134 quickly determines the θ and R values from the two crystal addresses in each coincidence data packet and increments the count of the corresponding sinogram array element. At the completion of an acquisition period, memory 136 stores the total number of annihilation events which occurred along each ray (R, θ) in the histogram.

Image CPU 140 controls the backplane bus 142 and links the image reconstruction components 108 to the communication link 116. The IG processors 138 also connect to the bus 142 and operate under the direction of the image CPU 140. The data decomposer 162 sends image data to the IG processors 138 which process the rash image data, or the histogram data, from the memory module 136 as discussed below. The resulting image array may be stored in memory module 136 and is output by the image CPU 140 to the operator work station 104.

The operator work station 104 includes a CPU 144, a CRT display 146 and a keyboard 148. The CPU 144 connects to the communications link 116 and scans the key board 148 for input information. Through the keyboard 148 and associated control panel switches, an operator can control calibration of the PET scanner system 100, its configuration, and the positioning of a patient table (not illustrated) during data acquisition.

Figure 5:
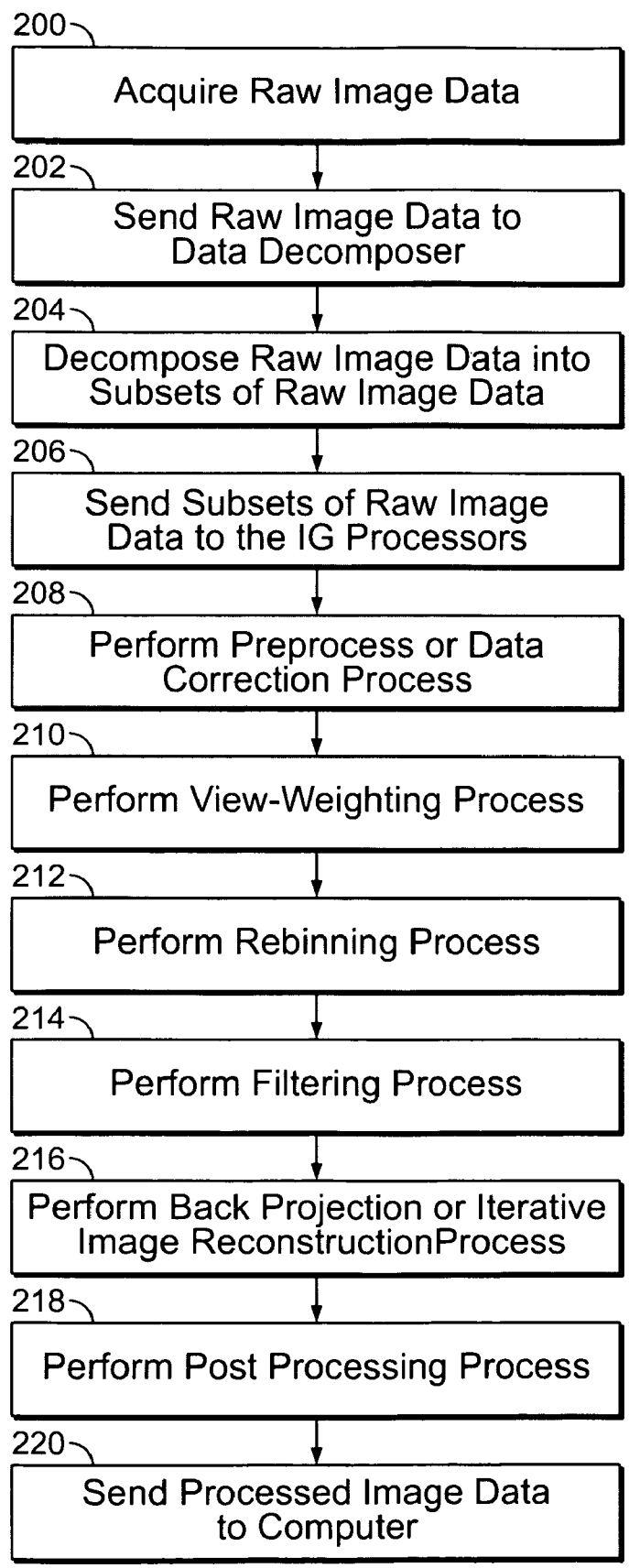
FIG. 5 illustrates a method for image reconstruction using data decomposition in accordance with an embodiment of the present invention.
Figure 6:
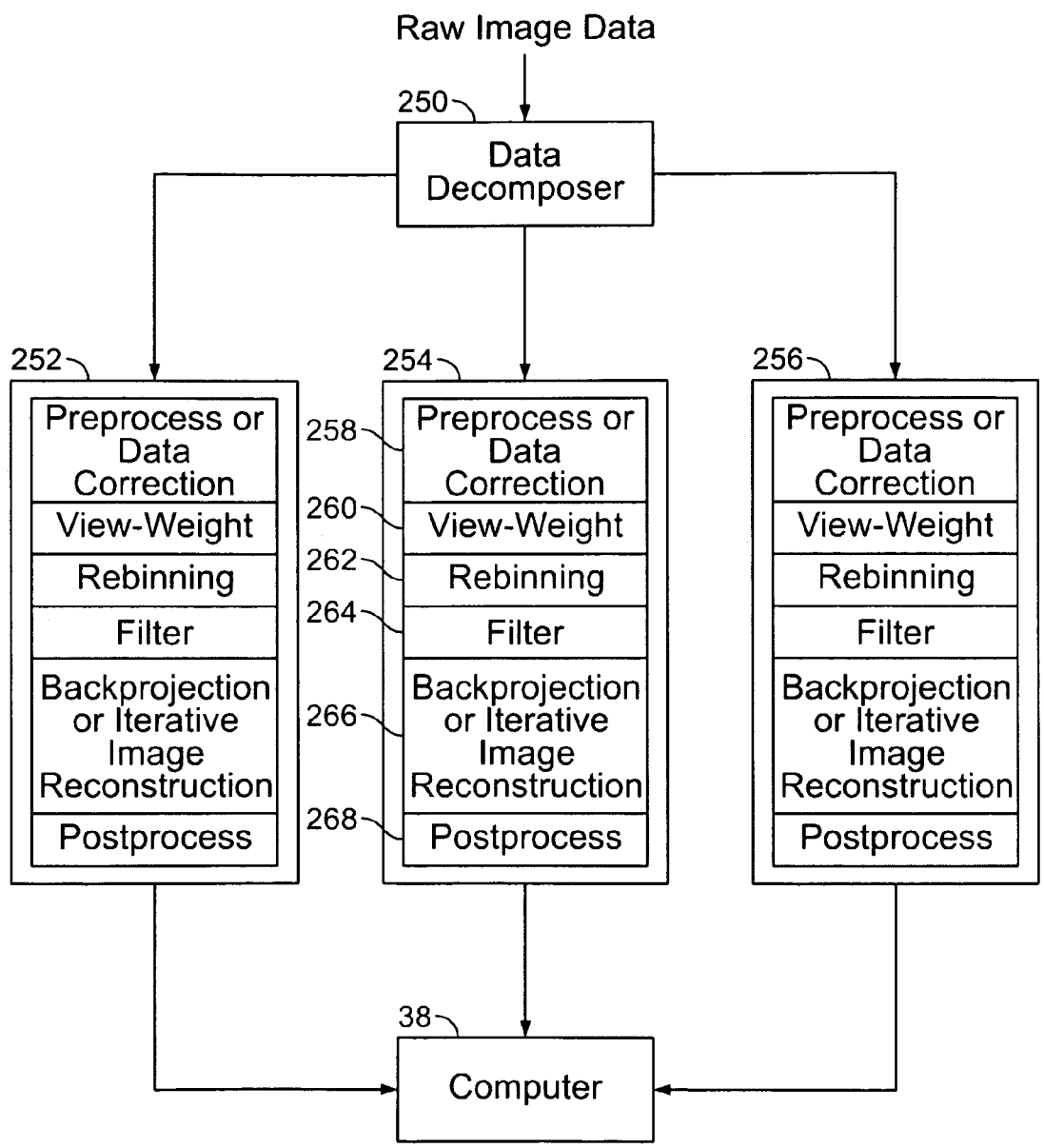
FIG. 6 illustrates a data decomposition and image generation process model formed in accordance with an embodiment of the present invention.

FIG. 5 illustrates a method for image reconstruction using data decomposition in accordance with an embodiment of the present invention. FIG. 6 illustrates a data decomposition and image generation process model formed in accordance with an embodiment of the present invention. FIG. 6 comprises a data decomposer 250 and multiple IG processors 252-256. The IG processors 252-256 are functionally identical, allowing the architecture to be scaled to meet desired reconstruction performance parameters. This redundancy improves the reconstruction reliability as the system can meet functional requirements with as few as one operational IG processor 252-256. It should be understood that although only three IG processors 252-256 are illustrated, more IG processors 252-256 may be utilized. FIGS. 5 and 6 will be discussed together.

Turning to FIG. 5, in step 200, the acquisition system acquires raw image data representative of an object of interest, such as the patient 18. Acquisition systems such as the CT imaging system 10 and the PET scanner system 100 acquire raw image data as discussed previously. For example, the DAS 36 of the CT imaging system 10 has converted the raw image data into digital form, while the histogram data from the PET scanner system 100 may be stored in the memory module 136. By way of example only, the image data may comprise enough information to form 900 images or frames of data. It should be understood that it is not necessary to acquire all of the image data prior to beginning the decomposing and processing steps below. In addition, the method of FIG. 5 and process model of FIG. 6 are not limited to CT and PET image data, but may be utilized by other diagnostic systems such as Nuclear Medicine, Magnetic Resonance Imaging (MRI), Ultrasound, and the like.

In step 202, the raw image data is sent to a data decomposer 250. The data decomposer 250 may comprise hardware and/or software. Therefore, the data decomposer 250 may be a separate component, or may be included within the computer 38 and mass storage 44 (FIG. 2) or the image CPU 140 and memory 136 (FIG. 3). Therefore, the data decomposer 250 may be a process which is run by a separate processor, such as the computer 38 or image CPU 140. By way of example only, the data decomposer 250 may be a part of a data acquisition and reconstruction control module (DARC) of the CT imaging system 10.

In step 204, the data decomposer 250 decomposes, or divides, the raw image data. The raw image data may be decomposed into three substantially equal portions, or subsets of image data. Continuing the example above wherein image data to form 900 data frames is acquired, each of three subsets of raw image data may comprise 300 data frames. It should be understood that the raw image data may not be decomposed based on data frames, and that the example is for illustrative purposes only. The first subset may comprise the first 300 data frames, the second subset may comprise the next 300 data frames, while the third subset may comprise the last 300 data frames. In another example, if the raw image data comprises data information for 1000 frames of data, the first and second subsets may comprise 333 data frames apiece, while the third subset comprises 334 data frames. The data decomposer 250 decomposes the raw image data into a number N of subsets based on the number of available IG processors 252-256. In other words, the data decomposer 250 determines how many IG processors 252-256 are available and automatically reconfigures itself to utilize the available IG processors 252-256.

In step 206, the data decomposer 250 sends the subsets of raw image data to the IG processors 252-256. For example, the first subset of raw image data may be sent to the IG processor 252, the second subset of raw image data may be sent to the IG processor 254, and the third subset of raw image data may be sent to the IG processor 256. The IG processors 252-256 each receive the respective subset of raw image data and begin the image generation process.

By way of example only, the data decomposer 250 may identify a predefined amount of raw image data for each IG processor 252-256. Therefore, once the image acquisition has been started and a portion of the raw image data has been acquired and received by the data decomposer 250, a predefined amount of raw image data is sent to each IG processor 252-256. The data decomposer 250 receives and holds raw image data as it is acquired. Then, when an IG processor 252-256 becomes available, the data decomposer 250 sends an amount of raw image data to the available IG processor 252-256. For example, the data decomposer 250 may send an amount of raw image data substantially equivalent to half of the total raw image data currently acquired and waiting to be processed. When the next IG processor 252-256 becomes available, the data decomposer 250 may again divide the raw image data currently acquired and waiting to be processed into two substantially equal subsets and send one subset to the next available IG processor 252-256 for processing. In this manner, the IG processors 252-256 are each engaged with raw image data to process, and the time any one IG processor 252-256 is idle is minimized.

Alternatively, the data decomposer 250 may decompose the raw image data into a number N of subsets where N is less than the number of total IG processors 252-256. For example, if raw image data from a previous scan remains to be processed, the data decomposer 250 may designate a portion of the total number of IG processors 252-256 to continue processing the previous scan, and divide the raw image data from the current scan between the remaining IG processors 252-256.

The IG processors 252-256 reconstruct the raw image data based on a reconstruction mode, which defines how the raw image data is processed. The reconstruction mode may be determined by the type of scan being performed, the anatomy being scanned, the desired image output, and the like. Many different reconstruction modes exist, and each mode comprises processing steps to be accomplished, optionally in a defined order, which may be different with respect to other reconstruction modes. Therefore, the steps 208-220 of FIG. 5 discussed below are illustrative only. It should be understood that different steps, a different number of steps, and/or a different order of steps may be used in place of steps 208-220 to process the raw image data according to the desired reconstruction mode. By way of example only, the reconstruction mode may be an Iterative Bone Correction Algorithm used with the CT imaging system 10 or a CT attenuation correction used with the PET scanner system 100. The reconstruction mode may be input by a user through the console 42.

The IG processors 252-256 each process data independently with respect to each other. Thus, the IG processors 252-256 do not interact with each other, but rather operate in parallel. Also, as each of the IG processors 252-256 comprise the functional capability to process the raw image data independently, it is only necessary to have one IG processor 252-256. The IG processor 254 will be discussed below as an exemplary IG processor.

By way of example only, each of the IG processors 252-256 may comprise a "personal computer" or PC, having a motherboard, processors, and memory. Software processes are loaded in the memory and the processors process the raw image data according to the software processes. Therefore, each of the IG processors 252-256 may be a module, circuit board, or unit which is easily installed within the CT imaging system 10 and PET scanner system 100. As each of the IG processors 252-256 within an imaging system are substantially the same, more IG processors 252-256 may easily be added to the imaging system to increase the processing speed and capability.

In step 208, a preprocess or data correction process submodule 258 of the IG processor 254 processes the raw image data. For example, preprocessing may comprise normalizing the raw image data by applying corrections based on calibration data and offset data particular to the CT imaging system. Alternatively, the PET scanner system 100 may implement a data correction process in which calibration data or other knowledge of the PET scanner system 100 or patient 18 is used. For example, CT attenuation correction (CTAC) may be implemented for the PET scanner system 100, wherein CT images are used to obtain information about the patient's 18 anatomy and used to correct the image data acquired by the PET scanner system 100.

In step 210, a view-weight submodule 260 of the IG processor 254 processes the image data. An interpolation process is performed on views and rows to compensate for the scan acquisition mode (i.e. helical, cardiac for CT imaging system 10) wherein the desired weighting functions are based on the scan and reconstruction modes. The view-weight submodule 260 may generate view-weighting weights based on view-weighting parameters and applies the weights to the image data.

In step 212, the rebinning submodule 262 of the IG processor 254 performs rebinning of the image data. For example, the rebinning submodule 262 may perform an interpolation process on views and rows acquired by the CT imaging system 10 to transform image data from fan-beam data format to parallel-beam data format. Equal space rebinning may be applied by the rebinning submodule 262 to process either CT or PET image data, and Fourier rebinning may be implemented by the rebinning submodule 262 for PET image data to create a 2D data set from a 3D data set.

In step 214, a filter submodule 264 of the IG processor 254 filters the image data. The selected reconstruction filter may be based on the reconstruction mode or input by the user. The filter submodule 264 generates one or more Filters tables based on the Filter parameters and may access a preselected protocol or a reconstruction filter input by a user to generate the Filters tables. The filter submodule 264 may apply a mathematical filtration based on the Filters tables to the image data on a view basis in response to the selected reconstruction filter.

In step 216, a back projection or iterative image reconstruction submodule 266 of the IG processor 254 processes the image data. For example, in the CT imaging system 10, back projection of view data and summation into an image matrix may be performed. Alternatively, 2D or 3D iterative reconstruction methods for PET and CT may be implemented. In this case, one or more of the previous steps are optional, as filtering (step 214) is not required for iterative reconstruction techniques.

By way of example only, one or more additional submodules may be implemented if the desired reconstruction mode is the Iterative Bone Correction Algorithm. A reprojection submodule forms view data from image matrix data (step 216), then the iterative bone correction algorithm is applied.

In step 218, a post processing submodule 268 of the IG processor 254 performs additional processing on the image data, such as ring fix and image filters.

In step 220, the IG processor 254 sends the processed image data to the computer, such as computer 38 of FIG. 2. Similarly the IG processors 252 and 256 send processed image data to the computer 38. The processed image data may be displayed and/or archived, for example. The data decomposer 250 continuously monitors the status of each IG processor 252-256. When an IG processor 252-256 becomes available, the data decomposer 250 sends rack image data to the available IG processor 252-256 to be processed as discussed previously.

Therefore, it should be understood that each of the IG processors 252-256 comprise a copy of the entire image generation work flow which runs in parallel across the multiple IG processors 252-256. Performance is enhanced by reducing the image reconstruction times, and thus the overall time required for CT and PET studies. By adding additional IG processors 252-256, additional and/or more complex image reconstruction algorithms may be performed, improving image quality and/or quantity without negatively impacting the image reconstruction or exam times. Thus, the IG processors 252-256 provide improved performance, flexibility and reliability.

Alternatively, individual IG processors 252-256 may be directed, or configured via software, to support unique image generation process models, enabling simultaneous support for multiple image reconstruction modes. The reconfiguration of the IG processors 252-256 via software may be changed on the fly as the IG processors 252-256 are not dedicated to any particular image reconstruction mode.

For example, a first IG processor 252 may be directed to process raw image data from a first scan and a second IG processor 254 may be directed to process raw image data from a second scan wherein the IG processors 252 and 254 utilize different image generation process models. Alternatively, a first IG processor 252 may be directed to process raw image data using a first image reconstruction mode and a second IG processor 254 may be directed to process the same raw image data using a second image reconstruction mode. A third IG processor 256 may be directed to process raw image data in either of the first and second image reconstruction modes, operating in parallel with one of the first and second IG processors 254 and 256 on a subset of the same raw image data, directed to process raw image data according to a third image reconstruction mode, or to process raw image data from a different scan.

In addition, image reconstruction corrections specific to individual rows of data or processing multiple rows of data at one time can now be supported. Previously, processing speed may have been improved by processing a single row of data, which was then combined with other single rows into an image. By way of comparison, the IG processors 252-256 can process data from individual or multiple rows of data, providing more system flexibility and processing speed.

By utilizing the data decomposition model of FIG. 6, the system design of the image reconstruction process function is simplified, which enables faster development and improved maintainability. Adding new units to a diagnostic system is coordinated at a higher level compared to previous systems. For example, an IG processor 252-256 which is not functioning properly can easily be replaced or removed with minimal or no impact to the user of the diagnostic system.

As discussed previously, the processing flow illustrated within the IG processors 252-256 in FIG. 6 and described in FIG. 5 is exemplary, and the CT imaging system 10 and PET scanner system 100 utilize different processing flows to achieve different image processing modes. For example, an iterative loop including a subset of one or more submodules 258-268 may be needed. For example, for PET 3D iterative reconstruction a preprocessing step may be followed by an iterative reconstruction process having several different corrections.

Also, the image reconstruction processing flow may not utilize all of the submodules 258-268 described above. Some of the processing steps may be optional and thus any subset of the processing steps, in combination with additional steps if necessary, forms a valid image reconstruction process. Therefore, the image reconstruction processing flow may implement the submodules 258-268 in a different order, in combination with other submodules not specifically mentioned above, or also by excluding one or more of the submodules 258-268. For example, view-weight submodule 260 may be utilized only in specific applications for the PET image data. Volume CT may be accomplished by a first process flows of rebinning, filtering, and view-weighting; a second process flow of view-weighting, rebinning, and filtering; or a third process flow of filtering, rebinning, and view-weighting.

While the invention has been described in terms of various specific embodiments, those skilled in the art will recognize that the invention can be practiced with modification within the spirit and scope of the claims.

What is claimed is:

1. A method for reconstructing images, comprising:
obtaining raw data representative of an object of interest;
decomposing said raw data into N subsets of raw data wherein N is at least two;
processing said N subsets of raw data to reconstruct image data by utilizing at least two image generation processors to perform image processing on said raw data in parallel with respect to each other; and
applying at least one of calibration data and offset data to said raw data, said at least one of calibration and offset data being based on system correction data representative of an acquisition system used to acquire said raw data.

2. The method of claim 1, further comprising acquiring said raw data by an acquisition system, said acquisition system being one of computed tomography (CT), positron emission tomography (PET), Nuclear Medicine, Magnetic Resonance Imaging (MRI), and Ultrasound.

3. The method of claim 1, wherein N is based on a number of available image generation processors.

4. The method of claim 1, wherein said number of available said image generation processors being equal to N.

5. The method of claim 1, wherein said number of available image generation processors being greater than said N.

6. The method of claim 1, wherein said N subsets of raw data comprising substantially equal amounts of said raw data.

7. The method of claim 1, said processing step further comprising:
processing said raw data with a first said image generation processor according to a first reconstruction process; and
processing said raw data with a second said image generation processor according to a second reconstruction process, said first and second reconstruction processes being different.

8. The method of claim 1, further comprising acquiring the raw data utilizing a Positron Emission Tomography (PET) System, wherein at least on of image generation processors performs attenuation correction when reconstructing the image data.

9. A method for increasing the performance of a system for processing raw image data, comprising:
acquiring raw data representative of an object of interest;
dividing said raw data into subsets of raw data; and
processing at least one of said subsets of raw data with a number of image generation processors in parallel; and
said dividing step further comprising dividing said raw data based on the number of said image generation processors.

10. The method of claim 9, further comprising adding at least one additional image generation processor, said image generation processors processing said raw data in parallel with respect to each other.

11. The method of claim 9, further comprising:
adding at least one additional image generation processor, said image generation processors processing said raw data in parallel with respect to each other;
dividing said image generation processors into subsets of said image generation processors; and
directing said subsets of said image generation processors to process said raw data according to different image generation process models.

12. The method of claim 9, said subsets of raw data being predefined substantially equal amounts of raw data.

13. An apparatus for processing raw data, comprising:
a data decomposer for dividing raw data acquired by a data acquisition system; and
at least two image generation processors for processing said raw data in parallel with respect to each other, wherein the data decomposer receives and holds the raw data as acquired, once the data decomposer receives a predefined amount of the raw data, the data decomposer sends the predefined amount of the raw data to an available one of the image generation processors.

14. The apparatus of claim 13, said data decomposer further comprising dividing said raw image data into N subsets of raw image data, wherein N equals an available number of said at least two image generation processors.

15. The apparatus of claim 13, wherein said at least two image generation processors being substantially identical.

16. The apparatus of claim 13, wherein said data decomposer identifying an available image generation processor, said data decomposer sending said available image generation processor a portion of said raw image data.

17. The apparatus of claim 13, wherein said image acquisition system further comprising one of a positron emission tomography (PET) acquisition system for acquiring raw PET image data and a computed tomography (CT) acquisition system for acquiring raw CT image data, said image generation processors outputting processed image data based on said raw PET image data and said raw CT image data, respectively.

18. The apparatus of claim 13, wherein a first image generation processor performs attenuation correction and second and third image generation processors perform iterative image reconstruction.

* * * * *